United States Patent [19]

Houbion

[11] 4,128,576
[45] Dec. 5, 1978

[54] O-AROYLVINYL BENZOYL CHLORIDES

[75] Inventor: John A. Houbion, Kirkwood, Mo.

[73] Assignee: Monsanto Company, St. Louis, Mo.

[21] Appl. No.: 867,722

[22] Filed: Jan. 3, 1978

[51] Int. Cl.$^2$ .............................................. C07C 63/10
[52] U.S. Cl. ................................... 260/544 D; 71/115
[58] Field of Search ..................................... 260/544 D

[56] References Cited

U.S. PATENT DOCUMENTS

| | | | |
|---|---|---|---|
| 3,240,792 | 1/1966 | Patrick et al. | 260/544 D |
| 3,580,910 | 5/1971 | Thiel et al. | 260/544 D |
| 3,709,938 | 1/1973 | Houlihan | 260/544 D |

OTHER PUBLICATIONS

Chemical Abstracts, vol. 74, 75,985(k) (1971).

*Primary Examiner*—Gerald A. Schwartz
*Attorney, Agent, or Firm*—Arnold H. Cole; Donald W. Peterson

[57] ABSTRACT

Certain novel o-aroylvinyl benzoyl chlorides have been found to possess herbicidal activity against various undesirable plant species.

14 Claims, No Drawings

O-AROYLVINYL BENZOYL CHLORIDES

This invention relates to a class of novel organic chemical compounds and to the preparation thereof. More particularly, the invention is concerned with certain o-aroylvinyl benzoyl chlorides which have been found to possess herbicidal activity against various undesirable plant species.

The o-aroylvinyl benzoyl chlorides of this invention have the formula

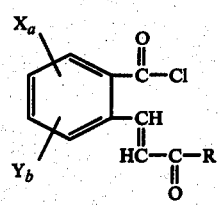

wherein X is halogen, Y is lower alkoxy or alkyl, nitro or trifluoromethyl, a is zero to 4, b is zero to 2, the sum of a + b is zero to 4, and R is phenyl, naphthyl or substituted phenyl, there being from 1 to 3 substituents selected from lower alkyl, lower alkoxy, halogen, $CF_3$, and nitro. As employed herein, "lower" designates the straight and branched chains of up to 4 carbon atoms. Preferred compounds of this invention are those wherein a and b are both zero. More particularly preferred are those compounds wherein R is other than naphthyl.

The novel compounds of the above formula are prepared by reacting thionyl chloride with a 3-phenacylphthalide or 3-(naphthoylmethylene)phthalide, preferably in the presence of an inert organic solvent. Equimolar amounts of reactants are generally employed, although a molar excess of thionyl chloride can be added. When a solvent is present, it is preferred to use benzene, a chlorinated hydrocarbon such as chloroform, carbon tetrachloride, methylene chloride or ethylene dichloride, or an ether such as diethyl ether or tetrahydrofuran. The reaction is most conveniently carried out with heating to the reflux temperature.

It will be recognized that the phthalide starting materials contain an asymetric carbon atom and hence may exist in two stereoisomeric forms. Both stereoismeric forms, together with mixtures thereof, fall within the scope of the reactants which can be employed to prepare the compounds of this invention. A great number of such 3-substituted phthalides are described in U.S. Pat. No. 3,407,206.

The following illustrative, non-limiting examples will serve to further demonstrate to those skilled in the art the manner in which specific compounds within the scope of this invention can be prepared.

EXAMPLE 1

A mixture of 26.25 grams (89 mmol) of 3-(2',4',6'-trimethylphenacyl)phthalide, 100 ml of thionyl chloride and a few drops of dimethylformamide was heated on a steambath for about 1 hour. The excess thionyl chloride was distilled off, 100 ml of toluene was added, and the solution was concentrated under vacuum. The residue was recrystallized from toluene/ligroin to yield 19 grams of o-(2',4',6'-trimethylbenzoylvinyl benzoyl chloride, m.p. 98°-99° C. Analysis gives 72.89% carbon and 5.59% hydrogen as against calculated values of 72.96% and 5.48% for $C_{19}H_{17}ClO_2$.

By substituting 3-(α-naphthoylmethylene)phthalide as the initial reactant in the above example, the product obtained is o-(α-naphthoylvinyl)benzoyl chloride. Similarly, when the initial reactant is 3-(4'-methoxyphenacyl)phthalide, the product obtained is o-(4'-methoxybenzoylvinyl)benzoyl chloride. Further, when said initial reactant is 6-chloro-3-phenacylphthalide, the product obtained is 5-chloro-2-benzoylvinyl benzoyl chloride.

EXAMPLE 2

A 500 ml flask fitted with a reflux condenser was charged with 29.7 grams (0.1 mol) of 3-(4-nitrophenacyl)phthalide, 0.12 mol of freshly distilled thionyl chloride and 100 ml of benzene. The mixture was heated to reflux temperature on a steambath, and a clear solution formed on initiation of refluxing, with evolution of HCl. The evolution ceased after 1 hour, after which benzene and excess unreacted thionyl chloride were distilled off under reduced pressure. The residual solid in the flask was triturated with ligroin, filtered and dried to yield o-(4'-nitrobenzoylvinyl)benzoyl chloride, m.p. 133°-134° C. Analysis shows 59.4% carbon, 3.36% hydrogen, 4.56% nitrogen and 11.72% chlorine as against calculated values of 60.87%, 3.19%, 4.44% and 11.23% for $C_{16}H_{10}ClNO_4$.

By substituting 3-(3'-trifluoromethylphenacyl)phthalide as the initial reactant in the above example, the product obtained is o-(3'-trifluoromethylbenzoylvinyl)benzoyl chloride. Similarly, where the initial reactant is 5,6-dibromo-3-(4'-methoxyphenacyl)phthalide, the product obtained is 5,6-dibromo-2-(4'-methoxybenzoylvinyl)benzoyl chloride.

EXAMPLE 3

Following the procedures described in Example 2, 3-(2',5'-dichlorophenacyl)phthalide was employed as the starting material. The product obtained was o-(2',5'-dichlorobenzoylvinyl)benzoyl chloride, m.p. 111° C. Analysis shows 56.62% carbon, 2.68% hydrogen and 31.31% chlorine as against calculated values of 56.59%, 2.67% and 31.32% for $C_{16}H_9Cl_3O_2$.

EXAMPLE 4

Following the procedures described in Example 2, 3-(4'-methylphenacyl)phthalide was employed as the starting material. The product obtained was o-(4'-methylbenzoylvinyl) benzoyl chloride, m.p. 95° C. Analysis shows 68.63% carbon and 4.44% hydrogen as against calculated values of 71.71% and 4.60% for $C_{17}H_{13}ClO_2$.

EXAMPLE 5

Following the procedures described in Example 2, 3-(4'-chlorophenacyl)phthalide was employed as the starting material. The product obtained was o-(4'-chlorobenzoylvinyl) benzoyl chloride, m.p. 100°-101° C. Analysis shows 62.97% carbon, 3.34% hydrogen and 23.27% chlorine as against calculated values of 62.98%, 3.30% and 23.24% for $C_{16}H_{10}Cl_2O_2$.

By substituting 4,5,6,7-tetrachloro-3-phenacylphthalide as the initial reactant in the above example, the product obtained is 3,4,5,6-tetrachloro-2-benzoylvinyl benzoyl chloride. Similarly, when the initial reactant is 6-nitro-3-phenacylphthalide, the product obtained is 5-nitro-2-benzoylvinyl benzoyl chloride.

EXAMPLE 6

Following the procedures described in Example 2, 3-phenacylphthalide was employed as the starting material. The product obtained was o-benzoylvinyl benzoyl chloride, m.p. 90–92° C. Analysis shows 71.25% carbon, 4.22% hydrogen and 12.89% chlorine as against calculated values of 70.99%, 4.10% and 13.10% for $C_{16}H_{11}ClO_2$.

EXAMPLE 7

A 1 liter flask was charged with 32.2 grams (115 mmol) of 3-(2′,5′-dimethylphenacyl)phthalide, 200 ml of benzene and 50 ml of thionyl chloride. After heating at reflux on a steambath for 30 minutes, the solution was concentrated. The residue was triturated with ligroin to give 32.5 grams of o-(2′,5′-dimethylbenzoylvinyl)benzoyl chloride, m.p. 96°–98° C. Analysis shows 72.29% carbon, 5.07% hydrogen and 11.80% chlorine as against calculated values of 72.36%, 5.06% and 11.87% for $C_{18}H_{15}ClO_2$.

By substituting 5-trifluoromethyl-3-phenacylphthalide as the initial reactant in the above example, the product obtained is 4-trifluoromethyl-2-benzoylvinyl benzoyl chloride. Similarly, when the initial reactant is 5,6-dimethoxy-3-phenacylphthalide, the product obtained is 4,5-dimethoxy-2-benzoylvinyl benzoyl chloride.

EXAMPLE 8

The post-emergence herbicidal activity of various compounds of this invention is demonstrated as follows. The active ingredients are applied in spray form to 14–21 day-old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at various rates (kg per hectare) of active ingredient. The treated plants are placed in a greenhouse and the effects are observed and recorded after approximately 2 weeks.

There are 11 different plant species in each test pan. Six of these species are broadleaf plants including Canada thistle, cocklebur, velvetleaf, morningglory, lambsquarters and smartweed. The remaining five species are narrowleaf plants and include nutsedge, quackgrass, johnsongrass, downy brome and barnyardgrass. The observations are made in terms of percent injury to each treated plant species. The results with compounds of this invention are reported below, and it should be understood that where a figure is not given for any individual plant species, the percent injury observed was less that 25% at the rate noted.

Employing the compound of Example 1, injury of 25–49% is observed on smartweed at 11.2 kg/hectare. Employing the compound of Example 2, injury of 25–49% is observed on Canada thistle, cocklebur, morningglory and lambsquarters at 56 kg/hectare. Employing the compound of Example 3, injury of 25–49% is observed on cocklebur, velvetleaf, morningglory, lambsquarters and johnsongrass at 56 kg/hectare. Employing the compound of Example 4, injury of 25–49% is observed on velvetleaf and morningglory at 56 kg/hectare, while injury of 75–99% is observed on Canada thistle at the same rate. Employing the compound of Example 5, injury of 25–49% is observed on lambsquarters, smartweed and barnyardgrass at 11.2 kg/hectare. Employing the compound of Example 6, injury of 25–49% is observed on cocklebur, velvetleaf and morningglory at 56 kg/hectare. Employing the compound of Example 7, injury of 25–49% is observed on Canada thistle and cocklebur at 11.2 kg/hectare.

EXAMPLE 9

The pre-emergent herbicidal activity of various compounds of this invention is demonstrated as follows. A good grade of top soil is placed in aluminum pans and compacted to a depth of three-eighth to one-half inch from the top of each pan. A predetermined number of seeds or vegetative propagules of each of several plant species are placed on top of the soil in each pan and then pressed down. Herbicidal compositions (as described in Example 8) employing the active ingredients of this invention are applied by admixture with or incorporation in the top layer of soil.

In this method, the soil required to cover the seeds and propagules is weighed and admixed with a herbicidal composition containing a known amount of active ingredient. The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period the number of emerged plants of each species is noted and compared to an untreated control.

All of the tests for pre-emergent activity are at an application rate of 11.2 kg/hectare, and the same eleven plant species enumerated in Example 8 are used. Here again, no figure is given if the percent control of an individual species is less than 25%.

Employing the compound of Example 1, control of 25–49% is observed on Canada thistle and smartweed. Employing the compound of Example 2, control of 26–50% is observed on Canada thistle and lambsquarters. Employing the compound of Example 7, control of 50–74% is observed on downy brome, while control of 75–100% is observed on barnyardgrass. The compounds of Examples 3–6 did not show at least 25% control on any of the plant species at the test rate.

From the test results presented in Examples 8 and 9, it can be seen that the herbicidal activity of the compounds of this invention is selective in nature. Only certain particular plant species are found to be injured or controlled by each specific compound. In this regard it should be recognized that each individual plant species selected for the above tests is a representative member of a recognized family of plants.

The herbicidal compositions, including concentrates which require dilution prior to application to the plants, of this invention contain from 5 to 95 parts by weight of at least one active ingredient and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, all parts being by weight of the total composition. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The herbicidal compositions of this invention, particularly liquids and soluble powders, preferably contain as a conditioning agent one or more surface-active agents in amounts sufficient to render a given composition readily dispersible in water or in oil. The incorporation of a surfaceactive agent into the compositions greatly enhances their efficacy. By the term "surface-active agent" it is understood that wetting agents, dispersing agents, suspending agents and emulsifying agents are included therein. Anionic, cationic, non-ionic and amphoteric agents can be used with equal facility.

Preferred wetting agents are alkyl benzene and alkyl naphthalene sulfonates, sulfated fatty alcohols, amines or acid amides, long chain acid esters of sodium isethionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters or hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

Water dispersible powder compositions can be made containing one or more active ingredients, an inert solid extender and one or more wetting and dispersing agents. The inert solid extenders are usually of mineral origin such as the natural clays, diatomaceous earth and the like. Examples of such extenders include kaolinites, attapulgite clay and synthetic magnesium silicate. The water-dispersible powder of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform and usually contains from 5 to about 95 parts by weight active ingredient, from about 0.25 to 25 parts by weight dispersant, and from about 4.5 to 94.5 parts by weight of water.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example, fertilizers, phytotoxicants, antidotes and plant growth regulants, pesticides and the like and used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g., fertilizers, other phytotoxicants, etc., and applied in a single application.

When operating in accordance with the present invention, effective amounts of the benzoyl chlorides are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray. The application of herbicidal compositions to aquatic plants is usually carried out by adding the compositions to the aquatic media in the area where control of the aquatic plants is desired.

The application of an effective amount of the compounds of this invention to the plant is essential and critical for the practice of the present invention. The exact amount of active ingredient to be employed is dependent upon such factors as the particular plant species and stage of development thereof, as well as the specific compound employed. In foliar and soil treatments for the control of vegetative growth, the active ingredients are applied in amounts from about 11.2 to about 56 or more kilograms per hectare. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A compound of the formula

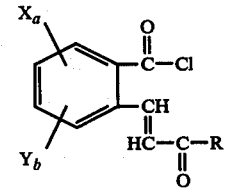

wherein X is halogen, Y is lower alkoxy or alkyl, nitro or trifluoromethyl, a is zero to 4, b is zero to 2, the sum of a + b is zero to 4, and R is phenyl, naphthyl or substituted phenyl, there being from 1 to 3 substituents selected from lower alkyl, lower alkoxy, halogen, $CF_3$ and nitro.

2. A compound as defined in claim 1 wherein a and b are zero.

3. A compound as defined in claim 1 wherein b is zero.

4. A compound as defined in claim 2 wherein R is phenyl.

5. A compound as defined in claim 2 wherein R is said substituted phenyl.

6. A compound as defined in claim 5 wherein R is p-chlorophenyl.

7. A compound as defined in claim 5 wherein R is p-nitrophenyl.

8. A compound as defined in claim 5 wherein R is p-tolyl.

9. A compound as defined in claim 5 wherein R is 2,5-dichlorophenyl.

10. A compound as defined in claim 5 wherein R is 2,5-dimethylphenyl.

11. A compound as defined in claim 5 wherein R is 2,4,6-trimethylphenyl.

12. A process for preparing a compound of the formula

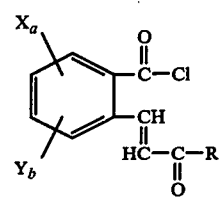

wherein X is halogen, Y is lower alkoxy or alkyl, nitro or trifluoromethyl, a is zero to 4, b is zero to 2, the sum of a + b is zero to 4, and R is phenyl, naphthyl or substituted phenyl, there being from 1 to 3 substituents selected from lower alkyl, lower alkoxy, halogen and nitro, which comprises reacting thionyl chloride with a phthalide of the formula

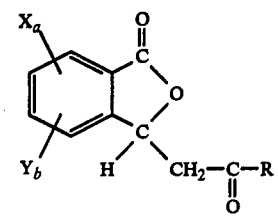

wherein X, a, b and R have the same meaning as above.

13. A process as defined in claim 12 wherein the reaction is conducted in the presence of an inert organic solvent.

14. A process as defined in claim 13 wherein the reactants are heated at reflux temperature.

* * * * *